(12) United States Patent
Jin et al.

(10) Patent No.: US 10,736,953 B2
(45) Date of Patent: Aug. 11, 2020

(54) STABLE, SPRAY DRIED, IMMUNOGENIC, VIRAL COMPOSITIONS

(71) Applicant: International AIDS Vaccine Initiative, Inc., New York, NY (US)

(72) Inventors: Tom Jin, New York, NY (US); Eric I-Fu Tsao, New York, NY (US)

(73) Assignee: International AIDS Vaccine Initiative, Inc., New York, NY (US)

(*) Notice: Subject to any disclaimer, the term of this patent is extended or adjusted under 35 U.S.C. 154(b) by 0 days.

(21) Appl. No.: 16/237,941

(22) Filed: Jan. 2, 2019

(65) Prior Publication Data

US 2019/0328862 A1  Oct. 31, 2019

Related U.S. Application Data

(63) Continuation of application No. 15/438,881, filed on Feb. 22, 2017, now abandoned, which is a continuation of application No. 13/321,048, filed as application No. PCT/US2010/035521 on May 20, 2010, now Pat. No. 9,610,343.

(60) Provisional application No. 61/179,744, filed on May 20, 2009.

(51) Int. Cl.
| | |
|---|---|
| *A61K 9/19* | (2006.01) |
| *A61K 39/12* | (2006.01) |
| *C12N 7/00* | (2006.01) |
| *C12N 15/86* | (2006.01) |
| *A61K 39/04* | (2006.01) |
| *A61K 39/00* | (2006.01) |

(52) U.S. Cl.
CPC ............... *A61K 39/12* (2013.01); *C12N 7/00* (2013.01); *C12N 15/86* (2013.01); *A61K 2039/5252* (2013.01); *A61K 2039/5256* (2013.01); *C12N 2710/10334* (2013.01); *C12N 2710/10343* (2013.01); *C12N 2710/10351* (2013.01); *C12N 2710/10361* (2013.01); *Y02A 50/386* (2018.01); *Y02A 50/412* (2018.01); *Y02A 50/466* (2018.01)

(58) Field of Classification Search
None
See application file for complete search history.

(56) References Cited

U.S. PATENT DOCUMENTS

2004/0042971 A1* 3/2004 Truong-Le ............... A01N 1/02 424/46
2009/0181078 A1* 7/2009 Reed .................... A61K 39/008 424/450

FOREIGN PATENT DOCUMENTS

| CN | 101287449 A | 10/2008 |
|---|---|---|
| WO | 2000-15262 | 3/2000 |
| WO | 2003-087335 | 10/2003 |
| WO | 2004-058156 | 7/2004 |
| WO | 2005123131 | 12/2005 |
| WO | 2007104562 | 9/2007 |

OTHER PUBLICATIONS

Corbanie et al., Vaccine, 2007, 25:8306-8317.*
Maa et al., Curr Drug Deliv. Jan. 2007;4(1):57-67.*
Croyle et al., Gene Ther. Sep. 2001;8(17):1281-90.*
Abdul-Fattah et al., "Drying-induced variations in physico-chemical properties of amorphous pharmaceuticals and their impact on stability II: Stability of a vaccine", Pharma. Res., 2007, 24(4):715-727.
Amorji et al., "Development of stable influenza vaccine powder formulations: Challenges and possibilities", Pharma. Res., 2008, 25(6):1256-1273.
Dilraj et al., "Response to different measles vaccine strains given by aerosol and subcutaneous routes to schoolchildren: a randomised trial", The Lancet, 2000, 355:798-803.
Maa et al., "Protein inhalation powders spray drying vs. spray freeze drying", Pharma Res., 1999, 16(2):249-254.
Radosevic et al., "Protective immune responses to a recombinant adenovirus type 35 tuberculosis vaccine in two mouse strains: CD4 and CD8 T-cell epitope mapping and role of gamma interferon", Infection and Immunity, 2007, 75(8): 4105-4115.
Magalhaes et al., "rBCG Induces strong antigen-specific T cell responses in rhesus macaques in a prime-boost setting with an adenovirus 35 tuberculosis vaccine vector", PLos One, 2008, 3(11):e3790.
Corbanie et al., "Spray drying of an attenuated live Newcastle disease vaccine virus intended for respiratory mass vaccination of poultry", Vaccine, 2007, 25(49):8306-8317.
Jin et al., "Stabilizing formulations for inhalable powders of an adenovirus 35-vectored tuberculosis (TB) vaccine (AERAS-402)", Vaccine, 2010, 28:4369-4375.
Maa et al., "Hepatitis-B surface antigen (HBsAg) powder formulation" process and stability assessment, Curr Drug Deliv., 2007, 4(1):57-67.

(Continued)

*Primary Examiner* — Nianxiang Zou
(74) *Attorney, Agent, or Firm* — Stradley Ronon Stevens & Young, LLP

(57) ABSTRACT

Viruses, and particularly genetically engineered, replication deficient viruses such as adenoviruses, poxviruses, MVA viruses, and baculoviruses which encode one or more antigens of interest, such as TB, malarial, and HIV antigens, are spray dried with a mannitol-cyclodextrin-trehalose-dextran (MCTD) to form a powder where the viability of the viruses are maintained at a suitable level for mass vaccinations after spray drying, and where the viability of the viruses are maintained at suitable level over a period of storage time, even in the presence of humidity.

15 Claims, 7 Drawing Sheets

(56) References Cited

OTHER PUBLICATIONS

Croyle et al., "Development of formulations that enhance physical stability of viral vectors for gene therapy", Gene Ther., 2001, 8(17):1281-90.

Corbanie et al., "Spray drying of an attenuated live Newcastle disease vaccine virus intended for respiratory mass vaccination of poultry", 2007, 25:8306-8317.

Croyle et al., "Development of formulations that enhance physical stability of viral vectors for gene therapy", Gene Therapy, 2001, 8:1281-1290.

Maa et al., "Hepatitis-B Surface Antigen (HB sAg) Powder Formulation: Process and Stability Assessment", Current Drug Delivery, 2007, 4:57-67.

\* cited by examiner

STABLE, SPRAY DRIED, IMMUNOGENIC, VIRAL COMPOSITIONS

BACKGROUND

Spray drying, whereby a liquid is transformed into dry powder particles by nebulization of droplets in hot drying air, has been recommended as an alternative to freeze drying for the preparation of inhalation products, as it represents an elegant one-step process for producing biopharmaceutical formulations with unique particle characteristics (see, Ameri M, Maa Y F (2006) *Drying Technology* 24: 763-768; Maa Y F, Nguyen P A, Swwwney T D, Shire S J, Hsu C C (1999) *Pharmaceutical Research* 16:249-254; Chen D, Maa Y F, Haynes J (2002) *Expert Vaccine Review* 1:265-276; and Broadhead J, Rouan S, Rhodes C (1992) *Drug Devel. Indust. Pharm* 18:1169-1206). Spray drying has the additional advantage of being a faster and more cost-effective dehydration process than freeze drying. Over the past decade, numerous protein delivery technologies have emerged, of which several are powder-based methods—such as microspheres for long-acting delivery, fine powders for pulmonary delivery, and biopharmaceutical/vaccine powders for intradermal delivery (see, Patton, J (1998) *Nat Biotechnol* 16:141-143; Dilraj A, Cutts F T, de Castro J F, Wheeler J G, Brown D, Roth C, Coovadia H M, Bennett J V (2000) *Lancet* 355: 798-803; Dilraj A, Sukhoo R, Cutts F T, and Bennett J V (2007) *Vaccine* 25:4170-4174; Philip V A, Mehta R C, Mazumder M K, DeLuca P P (1997) *Int J Phar* 151: 165-174; Chan H K, Clark A, Gonda I, Mumenthaler M, Hsu C (1997) *Pharm Res* 14:431-437; Martonen T, Katz I (1993) *J Aerosol Med* 6:251-274; Chew N Y K, Bagster D F, Chan H K (2000) *Int J Pharm* 206:75-83; Broadhead J, Rouan S, Hau I, Rhodes C (1994) *J Pharm and Pharm* 46:458-467; and Tzannis S T, Prestrelski S J (2000) *J Pharm Sci* 88:360-370). With the advent of these technologies, efforts to identify appropriate powder formation methods are increasing. It would be advantageous to have a stable powder formulation for viruses used in vaccines whereby the viruses survive spray drying procedures and storage. Also, it would be advantageous to have a stable, spray dried, dry powder formulation of viruses suitable for delivery by inhalation or other routes.

SUMMARY

The invention includes a method for stabilizing viruses in a spray dry powder, as well as to an immunogenic composition containing a virus in a mannitol-cyclodextrin-trehalose-dextran (MCTD) spray dried powder. Experiments have demonstrated that viruses survive spray drying and subsequent storage in powder form with MCTD at a rate which makes them viable as dry powder immunogenic compositions suitable for mass vaccinations.

Figure 1:
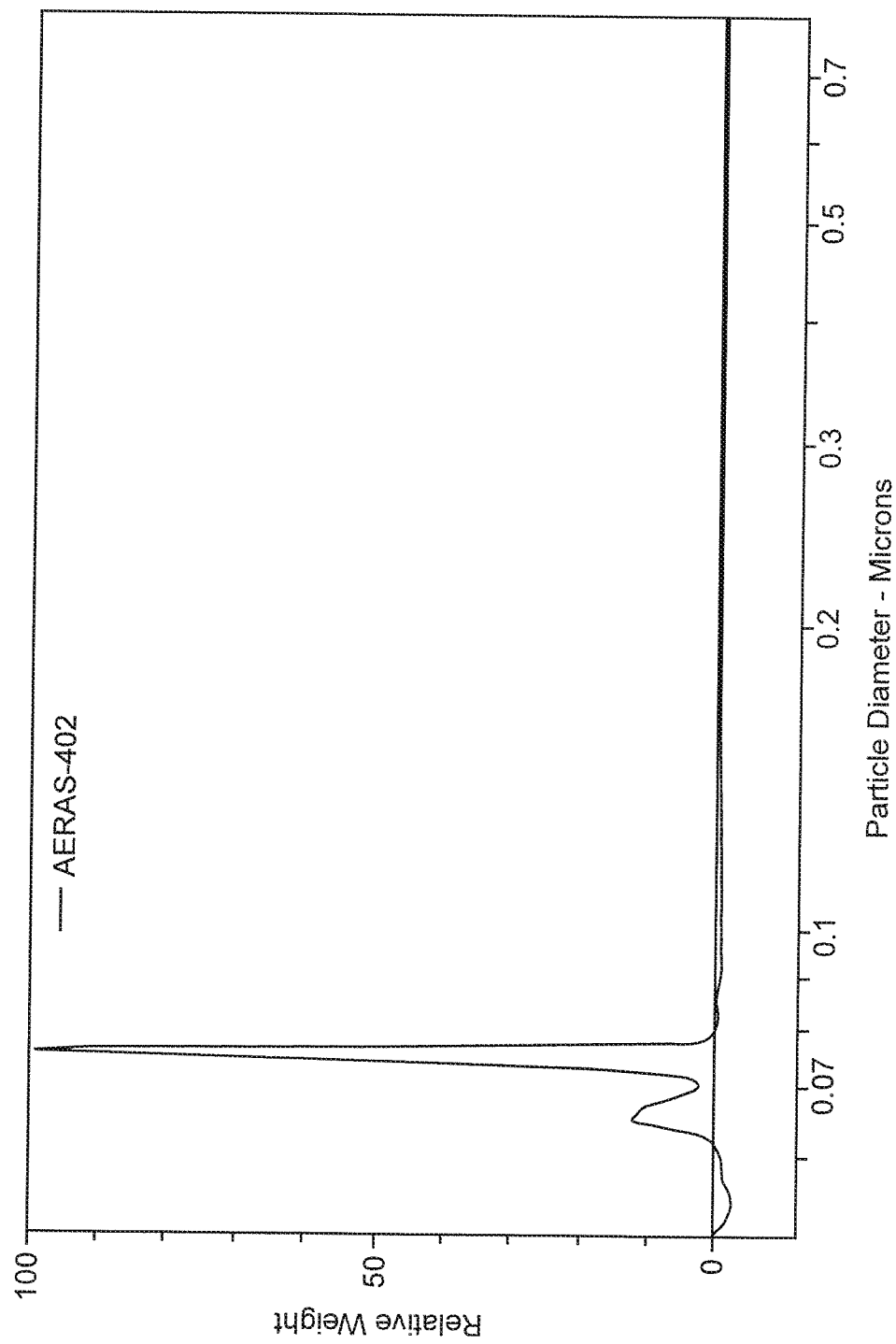
FIG. 1. The virus particle size distribution of rAd35.
The size of the rAd35 vaccine virus was measured by CPS Disc centrifuge. 8% and 24% sucrose in sample buffer were used for gradient solutions.
Figure 2A:
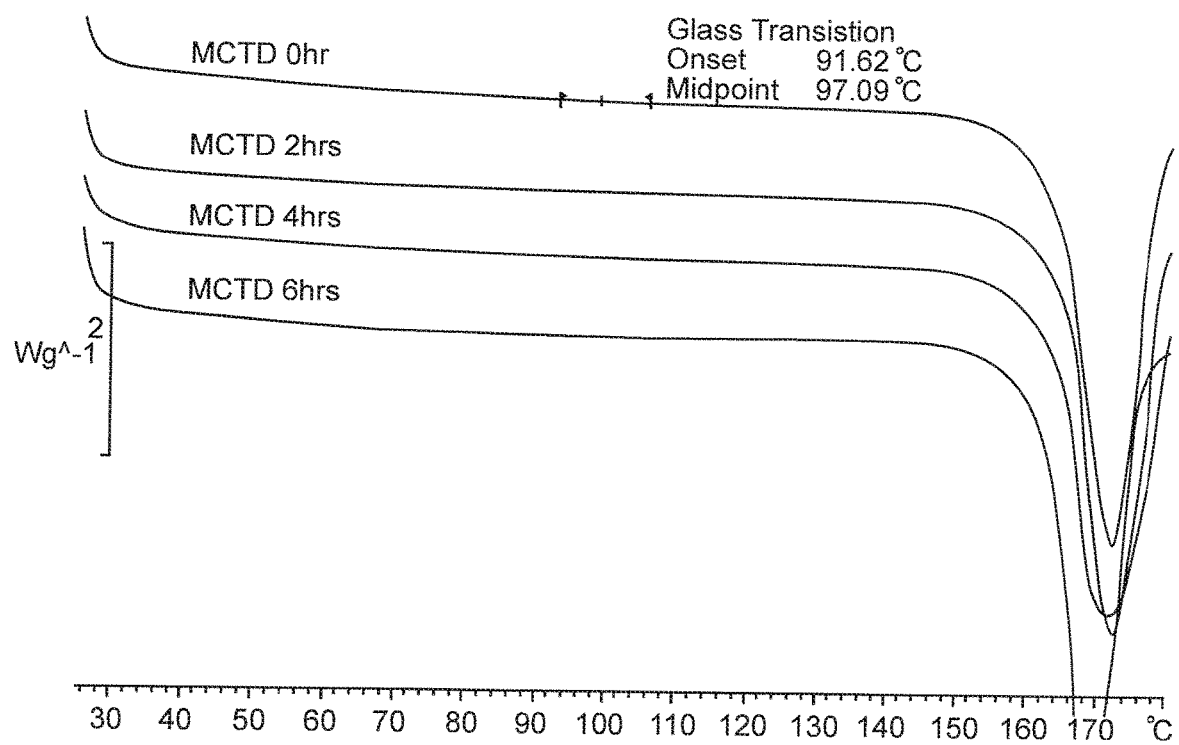
FIG. 2A. The glass transition temperature ($T_g$) of MCTD powder sample
Figure 2B:
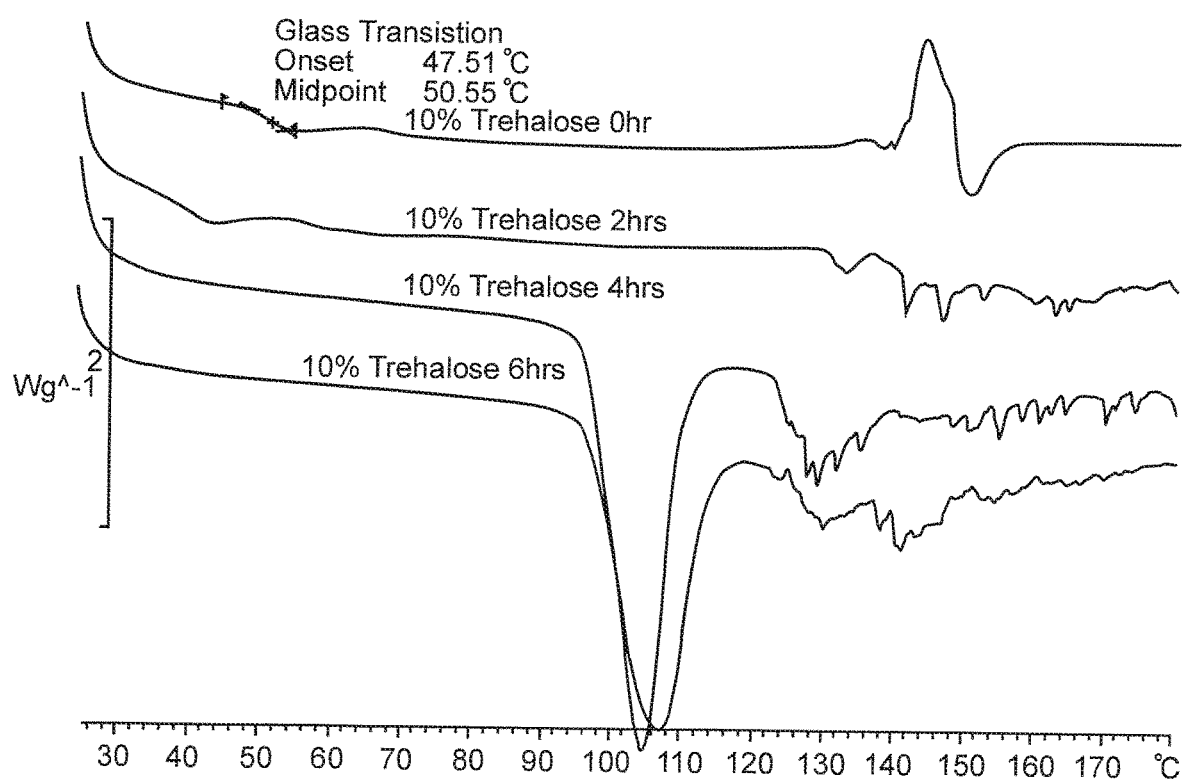
FIG. 2B. The glass transition temperature ($T_g$) of trehalose powder sample

For FIGS. 2A-B, the glass transition temperature (Tg) was determined by a DSC 823$^e$. The cover of the crucible was punched with a small hole before analysis. The sample (about 10 mg) was heated from 25° C. to 170° C. with a scanning rate of 10.0° C./min. The sample cell was purged with nitrogen gas at 10.0 ml/min.

Figure 3:
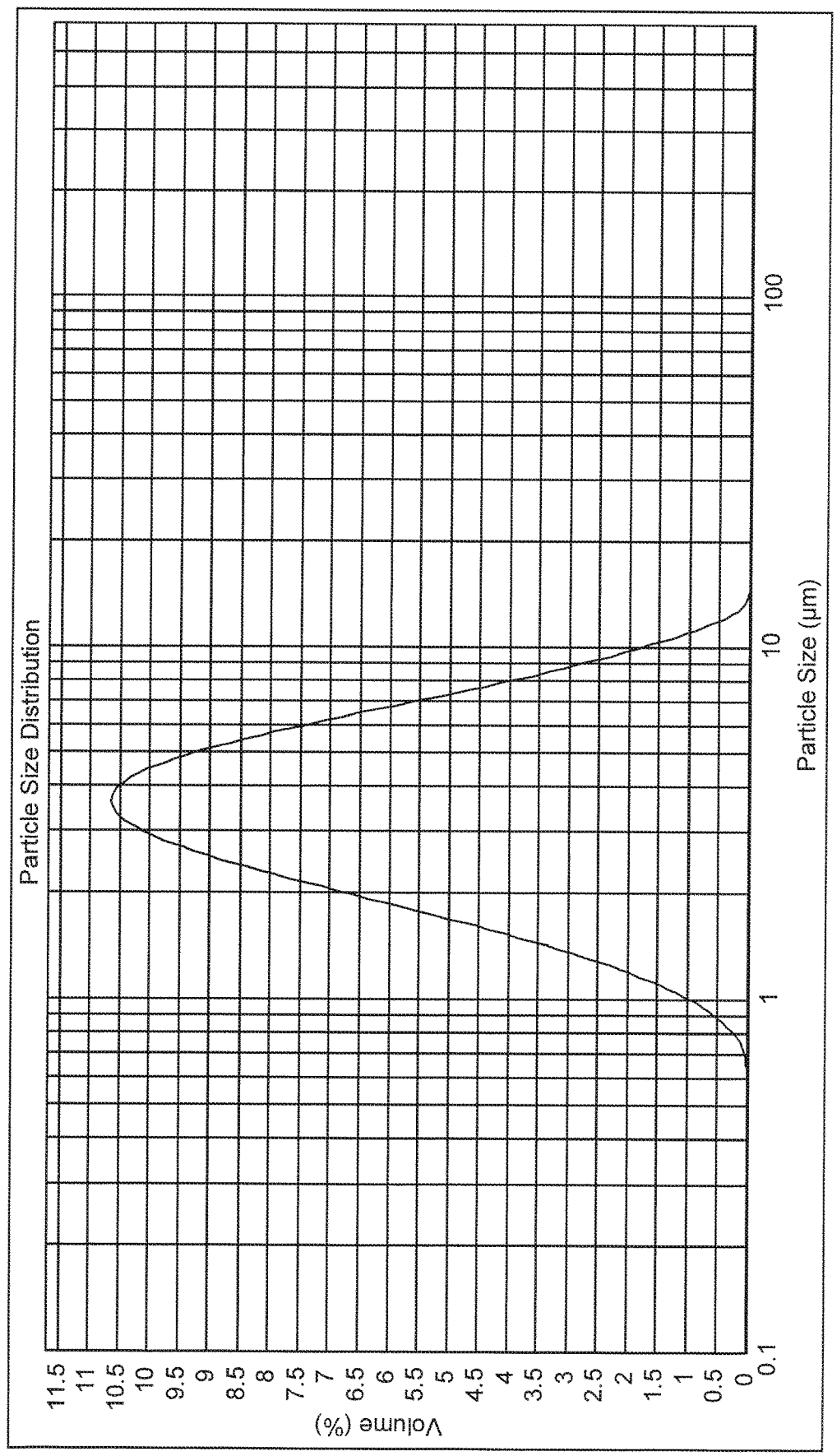

FIG. 3. The particle distribution of MCTD powder
Particle size distributions were measured by laser diffraction (Mastersizer 2000). The polydispersity of the powder was expressed by the span. Span=[D(v,90)−D(v,10)]/D(v,50), where D(v,90), D(v,10) and D(v,50) are the equivalent volume diameters at 90, 10 and 50% cumulative volume, respectively.

Figure 4A:
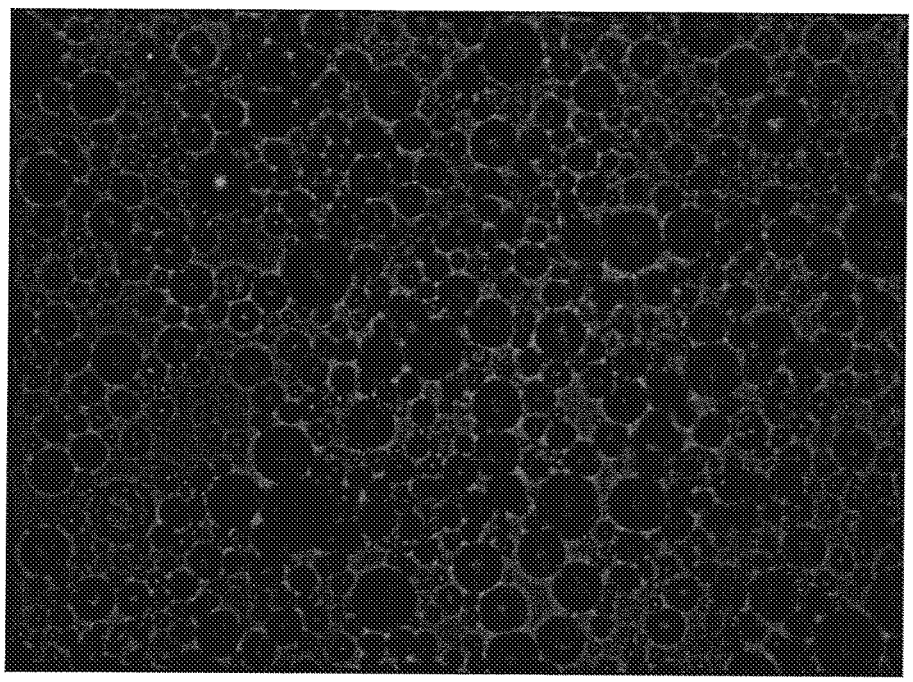

FIG. 4A. Microscope image (×1000) of particle generated from mannitol based formulation
The powder was re-suspended in anhydrous methanol at 20 mg/mL.

Figure 4B:
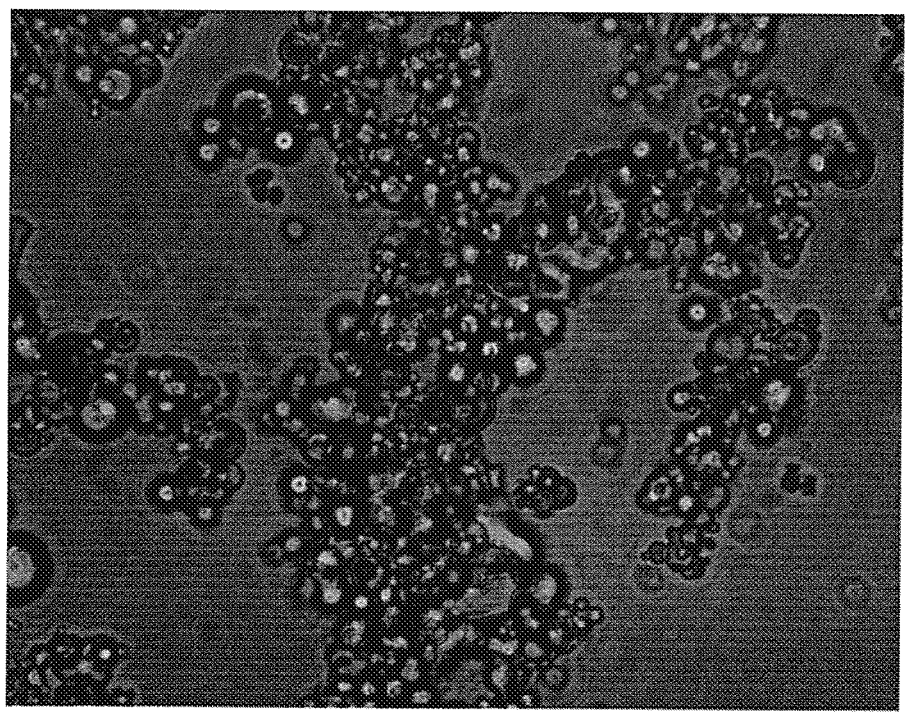

FIG. 4B. Microscope image (×1000) of particle generated from trehalose formulation
The powder was re-suspended in Halocarbon 0.8 oil at 20 mg/mL.

Figure 5:
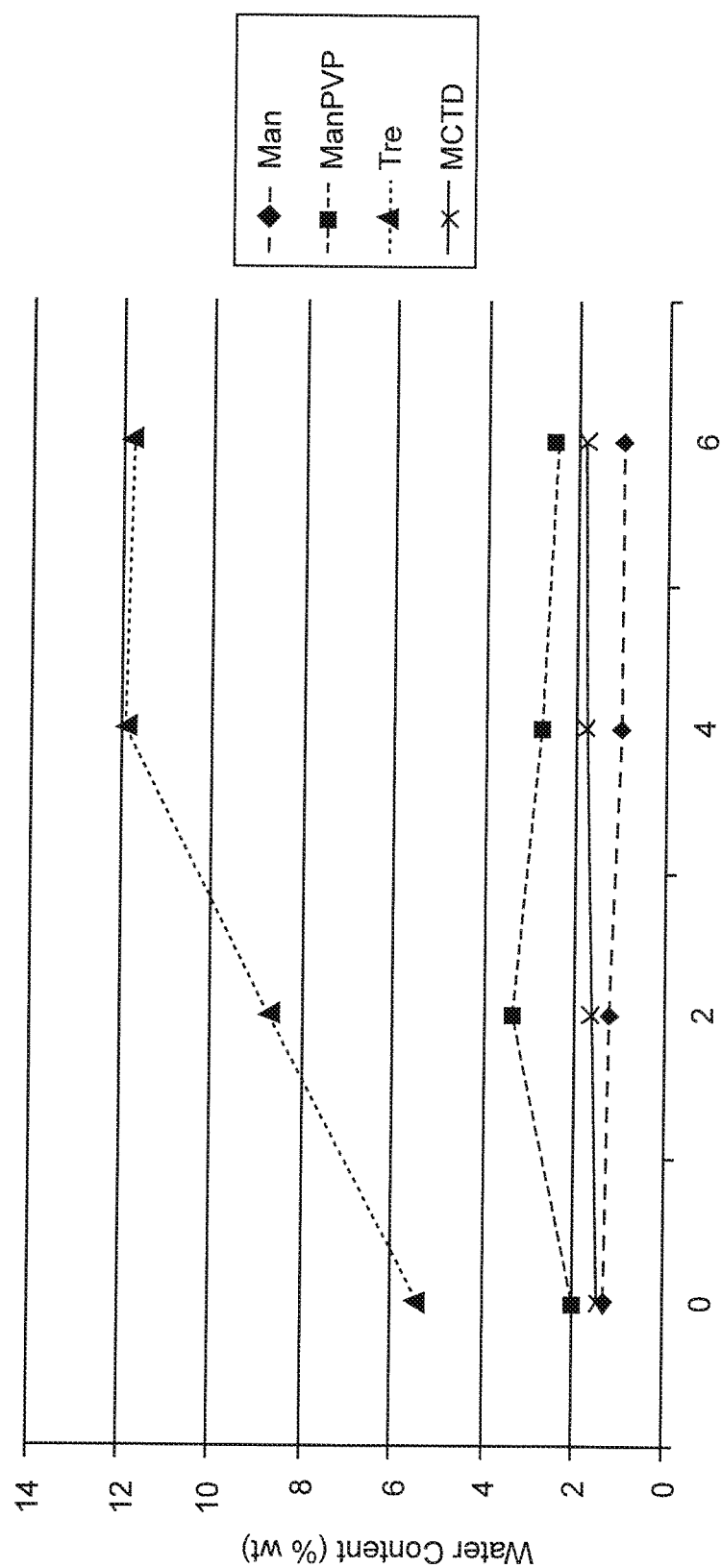

FIG. 5. Increase in water content of dry powder formulations exposed to 70% relative humidity FIG. 6. The $TCID_{50}$ recovery (log loss) of rAd35 in different formulations during spray drying process
The TCID50 recovery is expressed as the infectivity loss of rAd35 between pre spray drying and post spray drying samples. Titer changes are expressed in log loss per gram solid or powder. Man=mannitol; ManLeu=mannitol mixed with leucine; Tre=trehalose; Leu=leucine; ManSuc=mannitol mixed with sucrose; ManPBS=mannitol in PBS buffer; ManPVP=mannitol mixed with PVP; MCTD=mannitol-cyclodextrin-trehalose-dextran; ManIno=mannitol mixed with inositol; MTDT=mannitol-trehalose-dextran-tween 80.

Figure 7:
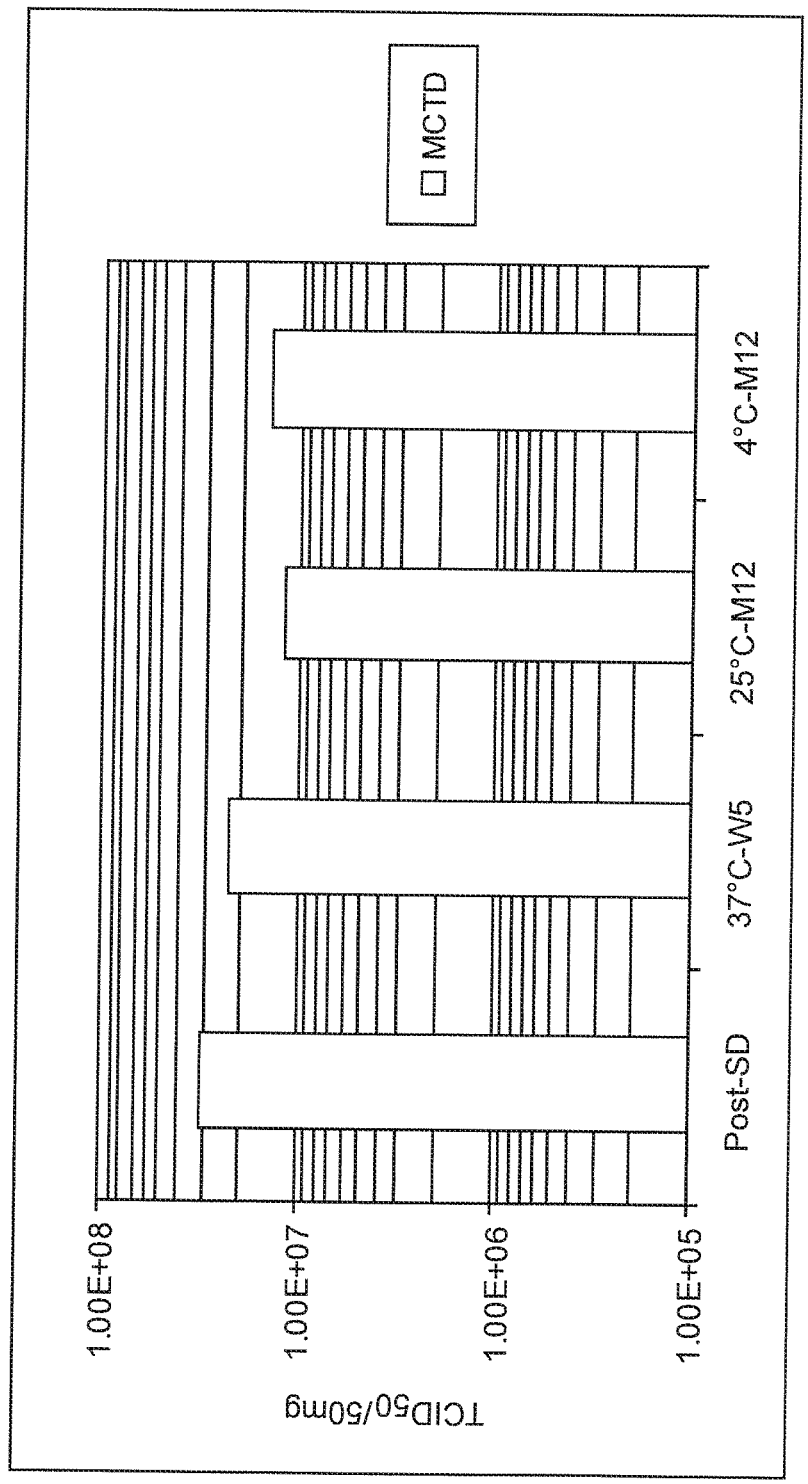

FIG. 7. The stability of rAd35 spray drying samples at 25° C. and 37° C.
The stability study of rAd35 spray lot with the candidate MCTD, was conducted for 1 month at both 25° C. and 37*C. The change in virus activity is expressed as log loss of virus infectivity by the $TCID_{50}$ test. Post-SD=post spray drying.

DESCRIPTION

Viruses are spray dried with a formulation of mannitol-cyclodextrin-trehalose-dextran (MCTD) to produce an immunogenic, spray dried, powder composition that is suitable for delivery by inhalation or other routes (e.g., oral, parenteral, intradermal, sublingual, etc.). The constituents of the MCTD formulation for spray drying are as follows:
M) Mannitol, present at 10-150 mg/ml, and more preferably at 50-100 mg/ml
C) Cyclodextrin, present at 0.1-10 mg/ml, and more preferably 0.2-1 mg/ml Preferably the cyclodextrin is β-Cyclodextrin; however, α- or γ-Cyclodextrin can be used, and mixtures of cyclodextrins may also be used.
T) Trehalose, present at 0.2-30 mg/ml, and more preferably at 0.5-5 mg/ml
D) Dextran, present at 0.1-30 mg/ml, and more particularly 0.5-5 mg/ml Preferably the molecular weight of the dextran is from 25K to 500K, and more preferably from 40K to 90K.
The MCTD formulation can include buffering agents (e.g., L-histidine at 1-20 mM (preferably 5-10 mM) and other stabilizers and excipients.

An exemplary contents of the formulation pre-spray drying is 100 mg/mL mannitol, 0.2 mg/mL cyclodextrin, 0.78 mg/mL (5 mM) histidine, 2 mg/mL trehalose and 1mg/mL dextran. The percent of active reagent (i.e., the virus (which can take the form of a genetically engineered viral vaccine vector)) in a pre-spray drying formulation would range from a $1E^4$/mL to $1 E^{11}$/mL, and often from $1 E^6$/mL to $1E^8$/mL (the content of virus being dosage related and dependent on choice of virus), and in a the final powder vaccine: the range is from viruse particle of $1E^4$/mg to $1 E^{10}$/mg.

As discussed in the Example below, a powder vaccine intended for aerosol delivery was formulated by spray drying rAd35 with a plurality of TB antigens with the aforementions MCTD mannitol-based stabilizers. Thermodynamic properties, water absorption, particle size distribution and morphology of the powders were evaluated and the virus survival during spray drying and storage was determined by medium Tissue Culture Infectious Dose ($TCID_{50}$). The MCTD mannitol-based powder had a narrow size distribution with a median volume diameter around 3.2-3.5 µm (suitable for human pulmonary vaccination of human) and good aerosolization characteristics. The spray dry powders generated from MCTD mannitol-based formulations were hydrophobic, which benefits virus survival during both production and storage at 4, 25 and 37° C. as compared to the hygroscopic formulations (trehalose, sucrose, dextran, PVP, leucine). The results in the Example demonstrates that it is possible to produce, in a one-step spray drying process, a stable dry powder formulation of, e.g., a TB vaccine, suitable for mass vaccination.

While the spray dried virus-MCTD powder is designed for use by inhalation, it should be understood that the powder can be combined with excipients for delivery by oral, parenteral, intradermal, and other routes. Suitable excipients are, for example, water, saline, dextrose, raffinose, glycerol, ethanol and the like, or combinations thereof. In addition, the composition may contain minor amounts of auxiliary substances such as wetting or emulsifying agents, pH buffering agents, and the like. The vaccine preparations of the present invention (i.e., the immunogenic compositions) may further comprise an adjuvant, suitable examples of which include but are not limited to Seppic, Quil A, Alhydrogel, etc.

If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of virus in the formulations may vary. However, in general, the amount in the formulations will be from about 1-99 percent. Further, the preparations of the present invention may contain a single type of virus or more than one type of virus (e.g., for vaccinating against multiple diseases simultaneously).

In the case of vaccine preparations, the present invention also provides methods of eliciting an immune response to antigens encoded by a genetically engineered vaccine vector, and methods of vaccinating a mammal against diseases or conditions associated with such antigens. By eliciting an immune response, we mean that administration of the vaccine preparation (i.e., immunogenic composition) of the present invention causes the synthesis in the subjects, post administration, of specific antibodies (at a titer in the range of 1 to $1\times10^6$, preferably $1\times10^3$, more preferable in the range of about $1\times10^3$ to about $1\times10^6$, and most preferably greater than $1\times10^6$) and/or cellular proliferation, as measured, e.g. by $^3$H thymidine incorporation. The methods involve administering a composition comprising the virus-MCTD spray dried powder in a pharmacologically acceptable carrier to a mammal (e.g., air or a propellant in the case of an inhalable formulation). I will be recognized that the virus-MCTD powder can be formulated into vaccine preparations that may be administered by any of the many suitable means which are well known to those of skill in the art, including but not limited to by injection, orally, intranasally, by ingestion of a food product containing the virus, etc. The targeted host is generally a mammal, and may be a human, although this need not always be the case, as veterinary applications are also contemplated.

The viruses employed in the practice of the invention can be simple attenuated viruses suitable for use as a vaccine such as polioviruses, rotaviruses, orthomyxoviruses such as influenza viruses, retroviruses such as RSV, poxviruses such as vaccinia, parvoviruses such as adeno associated viruses, papillomaviridae such as HPV, herpesviruses such as EBV, CMV or herpes simplex virus, lentiviruses such as HIV-1 and HIV-2, etc. Preferably, the viruses are non-replicating or are replication deficient (i.e., do not replicate or replicate at a low rate).

However, the invention has particular application to live, attenuated, recombinant viral vaccine vectors based on for example, adenoviruses, poxviruses, modified vaccinia Ankara (MVA) viruses, baculoviruses, recombinant vesicular stomatitis viruses (VSV), etc. The viral vaccine vector can take a variety of different forms, and will preferably be genetically engineered to encode one or more genes of interest, i.e. passenger genes or transgenes. The passenger genes are typically heterologous transgenes ("foreign" genes) that originate from another organism, such another virus, a bacteria or other pathogen, and may be from any organism. "Passenger gene" is intended to refer not only to entire "genes" but to any sequence that encodes a peptide, polypeptide, protein, or nucleic acid of interest, i.e. an entire "gene" per se may not be included, but rather the portion of a gene that encodes a polypeptide or peptide of interest e.g. an antigenic peptide. Further, various other constructions may be encoded by passenger genes, e.g. chimeric proteins, or various mutant (either naturally occurring or genetically engineered) forms of an amino acid sequence. In addition, totally artificial amino acid sequences that do not appear in nature may also be encoded. The viral vaccine vector is genetically engineered to contain one or more of such "passenger genes", and may also encode multiple copies of individual passenger genes. The viral vaccine vector functions as a vector to carry the passenger gene(s) and/or genes encoding suppression factors or other factors into host cells that are invaded by the viral vaccine vector, where the gene products are expressed, i.e. the gene sequences are expressible and transcription and/or translation of the gene products occurs within the host cell that is invaded by the bacterium. The sequences encoding the passenger genes and the genes encoding the suppression factors are operatively (operably) linked to expression control sequences, particularly expression control sequences that allow expression within the eukaryotic host cell. In some embodiments, if multiple passenger genes are encoded, each will have its own expression control system. In other embodiments, one expression control system will serve to drive expression of more than one passenger gene, e.g. as a single transcript with a plurality of gene sequences. Similarly, if multiple suppression factors are encoded in a viral vaccine vector, the transcription of each may be separately controlled, or multiple sequences may be under the control of one expression control sequence.

In particular, such passenger genes may encode one or more peptides or proteins that are antigens, and to which it is desired to elicit an immune response. Those of skill in the art will recognize that a wide variety of such antigens exists, including but not limited to those associated with infectious agents such as various viruses, bacteria, and fungi, etc. The viral pathogens, from which the viral antigens are derived, include, but are not limited to, Orthomyxoviruses, such as influenza virus (Taxonomy ID: 59771; Retroviruses, such as RSV, HTLV-1 (Taxonomy ID: 39015), and HTLV-II (Taxonomy ID: 11909), Papillomaviridae such as HPV (Taxonomy ID: 337043), Herpesviruses such as EBV Taxonomy ID: 10295); CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picomoviruses, such as Poliovirus (Taxonomy ID: 12080); Poxviruses, such as vaccinia (Taxonomy ID: 10245); Rotavirus (Taxonomy ID: 10912); and Parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. #183; Genbank accession # AF238278), Gag, Env (National Institute of Allergy and Infectious Disease HIV Repository Cat. #2433; Genbank accession # U39362), Tat (National Institute of Allergy and Infectious Disease HIV Repository Cat. #827; Genbank accession # M13137), mutant derivatives of Tat, such as Tat-31-45 (Agwale et al., *Proc. Natl. Acad. Sci. USA* 99:10037; 2002), Rev (National Institute of Allergy and Infectious Disease HIV Repository Cat. #2088; Genbank accession # L14572), and Pol (National Institute of Allergy and Infectious Disease HIV Repository Cat. #238; Genbank accession # AJ237568) and T and B cell epitopes of gp120 (Hanke and McMichael, *AIDS Immunol Lett.*, 66:177; 1999); (Hanke, et al., *Vaccine,* 17:589; 1999); (Palker et al., *J. Immunol.*, 142:3612 3619; 1989) chimeric derivatives of HIV-1 Env and gp120, such as but not restricted to fusion between gp120 and CD4 (Fouts et al., *J. Virol.* 2000, 74:11427-11436; 2000); truncated or modified derivatives of HIV-1 env, such as but not restricted to gp140 (Stamatos et al., *J Virol,* 72:9656-9667; 1998) or derivatives of HIV-1 Env and/or gp140 thereof (Binley, et al., *J Virol,* 76:2606-2616; 2002); (Sanders, et al., *J Virol,* 74:5091-5100 (2000); (Binley, et al. *J Virol,* 74:627-643; 2000), the hepatitis B surface antigen (Genbank accession # AF043578); (Wu et al., *Proc. Natl. Acad. Sci., USA,* 86:4726 4730; 1989); rotavirus antigens, such as VP4 (Genbank accession # AJ293721); (Mackow et al., *Proc. Natl. Acad. Sci., USA,* 87:518 522; 1990) and VP7 (GenBank accession # AY003871); (Green et al., *J. Virol.*, 62:1819 1823; 1988), influenza virus antigens such as hemagglutinin or (GenBank accession # AJ404627); (Pertmer and Robinson, *Virology,* 257:406; 1999); nucleoprotein (GenBank accession # AJ289872); (Lin et al., *Proc. Natl. Acad. Sci.,* 97: 9654-9658; 2000) herpes simplex virus antigens such as thymidine kinase (Genbank accession # AB047378; (Whitley et al., In: *New Generation Vaccines,* pages 825-854).

The bacterial pathogens, from which the bacterial antigens are derived, include but are not limited to: *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., *Bacillus anthracis* and *Borelia burgdorferi*. In particular, *Mycobacterium tuberculosis* antigens of interest include but are not limited to Rv0079, Rv0101, Rv0125, Rv0170, Rv0198c, Rv0211, Rv0227c, Rv0243, Rv0251c, Rv0282, Rv0283, Rv0284, Rv0285, Rv0286, Rv0287, Rv0288, Rv0289, Rv0290, Rv029, Rv0350, Rv0351, Rv0383c, Rv0384c, Rv0450c, Rv0467, Rv0468, Rv0503c, Rv0569, Rv0572c, Rv0574c, Rv0588, Rv0628c, Rv0685, Rv0754, Rv0798c, Rv0824c, Rv0847, Rv0867c, Rv0885, Rv1006, Rv1009, Rv1057, Rv1094, Rv1124, Rv1130, Rv1131, Rv1169c, Rv1174c, Rv1182, Rv1186c, Rv1187, Rv1188, Rv1196, Rv1221, Rv1347c, Rv1348, Rv1349, Rv1411c, Rv1436, Rv1461, Rv1462, Rv1464, Rv1465, Rv1466, Rv1477, Rv1478, Rv1594, Rv1636, Rv1733c, Rv1734c, Rv1735c, Rv1736c, Rv1737c, Rv1738, Rv1793, Rv1812c, Rv1813c, Rv1876, Rv1884c, Rv1886c, Rv1908c, Rv1926c, Rv1980c, Rv1986, Rv1996, Rv1997, Rv1998c, Rv2004c, Rv2005c, Rv2006, Rv2007c, Rv2008c, Rv2011c, Rv2028c, Rv2029c, Rv2030c, Rv2031c, Rv2032, Rv2110c, Rv2123, Rv2140c, Rv2182c, Rv2224c, Rv2244, Rv2245, Rv2246, Rv2251, Rv2377c, Rv2378c, Rv2380c, Rv2381c, Rv2382c, Rv2383c, Rv2386c, Rv2389c, Rv2428, Rv2429, Rv2430c, Rv2450c, Rv2457c, Rv2466c, Rv2510c, Rv2515c, Rv2516c, Rv2557, Rv2590, Rv2620c, Rv2621c, Rv2622, Rv2623, Rv2625c, Rv2626c, Rv2627c, Rv2628, Rv2629, Rv2657c, Rv2659c, Rv2660, Rv2710, Rv2744c, Rv2780, Rv2833c, Rv2856, Rv2869c, Rv2875, Rv2930, Rv2999, Rv3126c, Rv3127, Rv3129, Rv3130c, Rv3131, Rv3132c, Rv3133c, Rv3134c, Rv3139, Rv3140, Rv3173c, Rv3229c, Rv3250c, Rv3251c, Rv3283, Rv3290c, Rv3347c, Rv3372, Rv3406, Rv3516, Rv3546, Rv3570c, Rv3593, Rv3597c, Rv3616c, Rv3619c, Rv3660c, Rv3763, Rv3804c, Rv3812, Rv3833, Rv3839, Rv3840, Rv3841, Rv3871, Rv3873, Rv3874, Rv3875, Rv3876, Rv3878, and Rv3879c. (See also, U.S. patent application Ser. No. 11/945,680 to Shafferman et al., publication #20090136534, the complete contents of which are herein incorporated by reference.)

Examples of protective antigens of bacterial pathogens include the somatic antigens of enterotoxigenic *E. coli*, such as the CFA/I fimbrial antigen (Yamamoto et al., *Infect. Immun.*, 50:925 928; 1985) and the nontoxic B subunit of the heat labile toxin (*Infect. Immun.*, 40:888-893; 1983); pertactin of *Bordetella pertussis* (Roberts et al., *Vacc.*, 10:43-48; 1992), adenylate cyclase hemolysin of *B. pertussis* (Guiso et al., *Micro. Path.*, 11:423-431; 1991), fragment C of tetanus toxin of *Clostridium tetani* (Fairweather et al., *Infect. Immun.*, 58:1323 1326; 1990), OspA of *Borellia burgdorferi* (Sikand et al., *Pediatrics,* 108:123-128; 2001); (Wallich et al., *Infect Immun,* 69:2130-2136; 2001), protective paracrystalline-surface-layer proteins of *Rickettsia prowazekii* and *Rickettsia typhi* (Carl et al., *Proc Natl Acad Sci USA,* 87:8237-8241; 1990), the listeriolysin (also known as "Llo" and "Hly") and/or the superoxide dismutase (also know as "SOD" and "p60") of *Listeria monocytogenes* (Hess, J., et al., *Infect. Immun.* 65:1286-92; 1997); Hess, J., et al., *Proc. Natl. Acad. Sci.* 93:1458-1463; 1996); (Bouwer et al., *J. Exp. Med.* 175:1467-71; 1992), the urease of *Helicobacter pylori* (Gomez-Duarte et al., *Vaccine* 16, 460-71; 1998); (Corthesy-Theulaz, et al., *Infection & Immunity* 66, 581-6; 1998), and the *Bacillus anthracis* protective antigen and lethal factor receptor-binding domain (Price, et al., *Infect. Immun.* 69, 4509-4515; 2001).

The parasitic pathogens, from which the parasitic antigens are derived, include but are not limited to: *Plasmodium* spp., such as *Plasmodium falciparum*: (ATCC #: 30145); Trypanosome spp., such as *Trypanosoma cruzi* (ATCC #: 50797); *Giardia* spp., such as *Giardia* intestinalis (ATCC #: 30888D); *Boophilus* spp., *Babesia* spp., such as *Babesia microti* (ATCC #: 30221); *Entamoeba* spp., such as *Entamoeba histolytica* (ATCC #: 30015); *Eimeria* spp., such as *Eimeria maxima* (ATCC #40357); *Leishmania* spp. (Taxonomy ID: 38568); *Schistosome* spp., *Brugia* spp., *Fascida* spp., *Dirofilaria* spp., *Wuchereria* spp., and *Onchocerea* spp. (See also International patent application PCT/US09/30734 to Shaffermann et al., the complete contents of which is herein incorporated by reference.)

Examples of protective antigens of parasitic pathogens include the circumsporozoite antigens of *Plasmodium* spp. (Sadoff et al., *Science*, 240:336 337; 1988), such as the circumsporozoite antigen of *P. berghei* or the circumsporozoite antigen of *P. falciparum*; the merozoite surface antigen of *Plasmodium* spp. (Spetzler et al., *Int. J. Pept. Prot. Res.*, 43:351-358; 1994); the galactose specific lectin of *Entamoeba histolytica* (Mann et al., *Proc. Natl. Acad. Sci., USA*, 88:3248-3252; 1991), gp63 of *Leishmania* spp. (Russell et al., *J. Immunol.*, 140:1274 1278; 1988); (Xu and Liew, *Immunol.*, 84: 173-176; 1995), gp46 of *Leishmania major* (Handman et al., *Vaccine*, 18:3011-3017; 2000) paramyosin of *Brugia malayi* (Li et al., *Mol. Biochem. Parasitol.*, 49:315-323; 1991), the triose-phosphate isomerase of *Schistosoma mansoni* (Shoemaker et al., *Proc. Natl. Acad Sci., USA*, 89:1842 1846; 1992); the secreted globin-like protein of *Trichostrongylus colubriformis* (Frenkel et al., *Mol. Biochem. Parasitol.*, 50:27-36; 1992); the glutathione-S-transferase's of *Fasciola hepatica* (Hillyer et al., *Exp. Parasitol.*, 75:176-186; 1992), *Schistosoma bovis* and *S. japonicum* (Bashir et al., *Trop. Geog. Med.*, 46:255-258; 1994); and KLH of *Schistosoma bovis* and *S. japonicum* (Bashir et al., supra, 1994).

The viral vaccine vector may also be genetically engineered to express nucleic acid sequences that encode one or more proteins that interfere with mammalian host cell type I interferon (IFN) responses. Examples of proteins that modulate type I IFN response include non-structural protein 1 (NSP-1) from rotavirus, NS1 protein from influenza virus, and C12R from ectromlia virus. In addition, other suitable IFN modulating proteins include but are not limited to: Ebola VP35 (The Ebola virus VP35 protein functions as a type I IFN antagonist. CF Basler, X Wang, E Mühlberger, V Volchkov, *Proceedings of the National Academy of Sciences,* 2000. National Acad Sciences); Vaccinia B18R (Waibler et al. *Journal of Virology.* 2009 February; 83(4):1563-71); rabies phosphoprotein P (Krzysztof Brzózka, et al. *Journal of Virology*, March 2006, p. 2675-2683, Vol. 80, No. 6); lymphocytic choriomeningitis virus (LCMV) nucleoprotein (Martinez-Sobrido Luis et al. *Journal of Virology* 2006; 80(18):9192-9); and Hepatitis C virus (HCV) protease NS3/4A (Xiao-Dong Li, et al. *Proc Natl Acad Sci USA.* 2005 Dec. 6; 102(49): 17717-17722). In addition, Weber and Haller (*Biochemie* 89, 2007, 836-842) describe other examples of suitable proteins such as the E3L protein of poxviruses, the sigma3 protein of reoviruses, the USI 1 protein of herpes simplex virus, and murine cytomegalovirus proteins m142 and m143.

Alternatively, it may be desired to elicit an immune response to antigens that are not associated with infectious agents, for example, antigens associated with cancer cells, Alzheimer's disease, Type 1 diabetes, heart disease, Crohn's disease, multiple sclerosis, etc. The viral vaccine vectors of the present invention may also be genetically engineered with one or more passenger genes encoding for these types of antigens.

In addition, the passenger genes that are carried by the viral vaccine vector need not encode antigens, but may encode any peptide or protein of interest. For example, the methods of the invention can be used for the delivery of passenger molecules for correction of hereditary disorders, e.g. the vectors may be used for gene therapy. Such genes would include, for example, replacement of defective genes such as the cystic fibrosis transmembrane conductance regulator (CFTR) gene for cystic fibrosis; or the introduction of new genes such as the integrase antisense gene for the treatment of HIV; or genes to enhance Type I T cell responses such as interleukin-27 (IL-27); or genes to modulate the expression of certain receptors, metabolites or hormones such as cholesterol and cholesterol receptors or insulin and insulin receptors; or genes encoding products that can kill cancer cells such as tumor necrosis factor (TNF)-related apoptosis-inducing ligand (TRAIL); or a naturally occurring protein osteoprotegerin (OPG) that inhibits bone resorption; or to efficiently express complete-length humanized antibodies, for example, humanized monoclonal antibody that acts on the HER2/neu (erbB2) receptor on cancer cells.

In addition, the passenger genes may encode inhibitory RNAs such as "small inhibitory" siRNAs. As is known in the art, such RNAs are complementary to an mRNA of interest and bind to and prevent translation of the mRNA, e.g. as a means of preventing the expression of a gene product.

Preferably, the viral vaccine vector will be genetically engineered to express one or more proteins (i.e., antigens) or a fusion protein of multiple antigens which, when administered to a subject (e.g., a human or other animal (e.g., mammal), will result in an immune response to one or more infections, e.g., tuberculosis (TB), malaria, HIV, dengue fever, etc.

The construction of viral vaccine vectors is well known in the art. Generally, the genes that are placed into the viral vaccine vector via genetic engineering are under control of an expression sequence such as a promoter, internal ribosomal entry site (IRES), various enhancer sequences, etc. Such sequences and promoters may be naturally within the viral vaccine vector (i.e. native to the virus, e.g., adenovirus), and the sequences of interest placed at a location such that their expression is driven by the wildtype viral sequences. Alternatively, promoters from organisms other than viral vaccine vector (e.g., adenovirus) may be cloned into the virus, together with the gene(s) of interest. Exemplary promoters that may so utilized in the practice of the invention include but are not limited to various vira, prokaryotic or eukaryotic promoters, e.g. cytomegalovirus (CMV) promoters, cauliflower mosiac virus promoter, influenza and HV viral promoters, heat shock promoters (e.g. hsp60 promoter) and other promoters from *M. tuberculosis*, etc. Of these, both constitutive and inducible promoters may be utilized.

Example

Results

Vaccine Virus Particle Size

For the experiments a recombinant adenovirus (rAd35) particle expressing a plurality of TB antigens was used. rAd35 induces low levels of neutralizing antibodies in non-human primates which are an important model for preclinical vaccine trials since they are susceptible to Mtb infection and develop clinical features and a pathology which closely resembles TB in humans (see, Nanda et al. (2005) *J Virol* 79: 14161-14168, and McMurray D N (2000) *Clin Infect Dis* 30 Suppl 3: S210-212). As noted above, a variety of different viruses can be used, and a variety of different antigens, factors, and other nucleotide sequences can be encoded into a viral vaccine particle such as rAd35. The main size distribution peak of the tested rAd35 on the Disc centrifuge curve was around 77 nm (FIG. 1). There was a smaller peak of virus size of 65 nm. The two peaks did not shift even when the virus bulk material was concentrated 10 times (data not shown).

Thermodynamic Properties

Glass transition temperatures of the drying powders were determined after production and after storage at high humidity. The mannitol based powder (MCTD) had the highest $T_g$ value of 97.09° C., with a melting point of 166.53° C. for the crystalline mannitol component (FIG. 2A). The $T_g$ of trehalose powder after spray drying was 50.55° C. (FIG. 2B). Mannitol alone did not have a $T_g$ and Mannitol with PVP powder had a $T_g$ of 85.78° C. The thermodynamic curves and glass transition temperatures of representative spray powders are shown in Table 1.

TABLE 1

The characteristics of different spray drying powders

| Formula | $T_g$ (° C.) | Yield[1] (%) | d (0.5)[2] (VMD) | Moisture content[3] (%) |
|---|---|---|---|---|
| Mannitol | — | 30.0 | 3.1 | 1.28 |
| Mannitol with PVP | 85.78 | 19.9 | 7.0 | 1.94 |
| Trehalose | 50.55 | 6.0 | 2.6 | 5.40 |
| Leucine | — | 4.3 | — | 1.64 |
| MCTD | 97.09 | 35.3 | 3.2 | 1.45 |

[1]Powder yield was calculated by the wt/wt of pre and post spray drying solid. The total amount of pre-spray drying solid was determined from lyophilization weight of pre-spray drying mixture.
[2]d (0.5) is particle size at D (v, 50), which is the equivalent volume diameter at 50% cumulative volume. The particle size of the powders was described by the volume median diameter (VMD).
[3]The residual moisture contents were evaluated by a TIM550 Karl Fischer (Radiometer Analytical) in a dry box, the resulting water percents were expressed based on wt/wt.

Particle Size Distribution and Polydispersity

Spray drying the formulation of MCTD resulted in fine powder with an average particle size range of D(v,50)=3.2-3.5 μm. Combined with D(v,0.1) and D(v, 0.9), the span was around 1.5 μm. The percent of inhalable particles [IP, 1 μm<IP<5 μm] could reach to 72.6% of the total particles, and most powders are spherical (FIGS. 3 and 4A) (it being recognized that the powder can be provided to a subject by routes other than inhalation). The spray dried powder using the MCTD formation did not have either different distribution or thermodynamic properties in rAD35 and placebo tests (data not shown). The Mannitol with PVP formulation had a dry powder size of D(v, 50)=7.0 μm and the trehalose product had a D(v, 50)=2.6 μm (Table 1). Although the trehalose formulation had a smaller particle size after spray drying (Table 1 and FIG. 4B), the trehalose powder clumped easily after exposure to high humidity, and particle size could increase significantly which was not suitable for laser diffraction measurement. MCTD, however, did not have any detectable decrease in IP<5 μm, even after storage at 37° C. (for 28 days (results were the same as shown in FIG. 3).

Moisture Content and Shifting of Glass Transition Temperature

To compare the moisture content variations under high humidity (70%) of different formulations, we selected four representative powders prepared from placebo formulations under the same processing conditions. The water contents of post spray drying powders were: Mannitol 1.28%; Mannitol with PVP 1.94%; Trehalose 5.40%; and MCTD 1.45% (Table 1). The water absorption tendency was different between the trehalose and mannitol-based formulations (FIG. 5). After 2 hr in 70% humidity, the water content of trehalose powder increased 61% (from 5.40 to 8.70%, wt/wt), and after 4 hr, trehalose powder absorbed 37% more water. The total weight of water increased 120.9% (from 5.40 to 11.93%). The moisture saturation stage occurred after 4 hr for trehalose powder. The mannitol based formulations (Mannitol, Mannitol with PVP and MCTD) had high resistance to water absorption. Mannitol alone did not have any increase in moisture content during 6 hr under high humidity exposure, and MCTD powder only increased from 1.45 to 1.80% in water content during this period.

After exposure at high humidity of 70%, the $T_g$ of mannitol based powder (MCTD) did not show significant change within 6 hr. Trehalose powder, however, showed apparent difference in thermodynamic properties: first, after 2 hr exposure at high humidity, its $T_g$ shifted down to 38.76° C. then, after 4 and 6 hr the melting point was reduced to around 102° C. (FIG. 2B), and the exposed powder appeared crystallized.

Recovery and Stability of Different Spraying Lots

Figure 6:
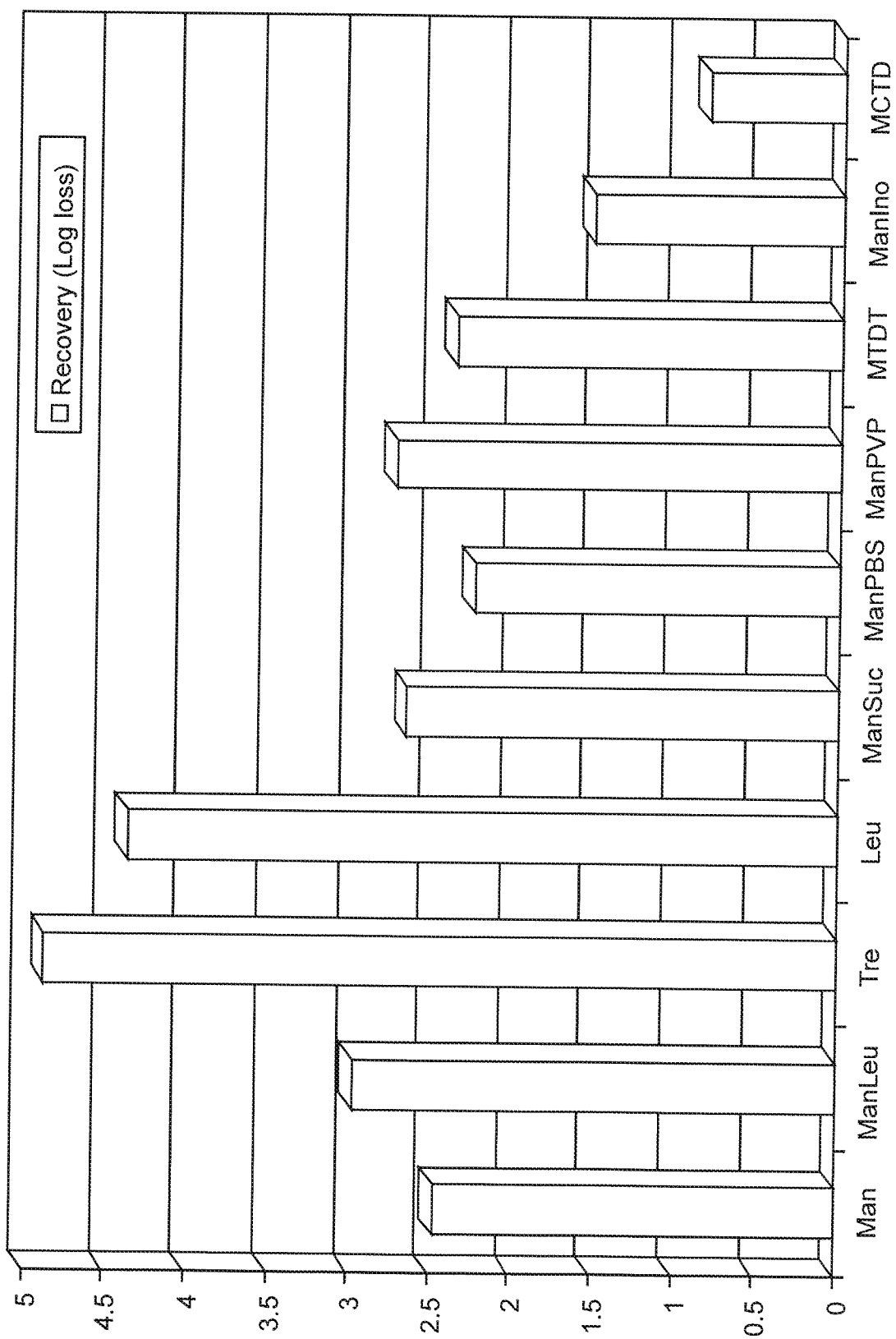

The effect of spray drying on the infectivity of rAd35 in 10 different formulations is shown in FIG. 6, where the titer before drying is compared with the titer after spray drying. The titer changes were expressed in log loss per gram solid or powder. The total amount of pre-spray drying solid was from the weight of lyophilization of the pre-spray drying mixture.

All formulations except MCTD suffered at least a 1.5 (maximum 4.9) log loss of the viral activity. For the MCTD formulation, the loss in virus titer after spray drying was only 0.83 log. The largest decreases in virus activity by median Tissue Culture Infective Dose ($TCID_{50}$) test were for the trehalose and leucine formations. Although adding sucrose, inositol, or PVP, or adding PBS buffer could increase the survival of virus during the spray drying process, the $TICD_{50}$ of live rAd35 was still over 1 log decreased at the end of preparation. Most formulations also resulted in low yield at less than 10%, while mannitol-based formulations could reach more than 30% solid yield at the end of spray drying processing (partial data shown in Table 1).

The stability study of rAd35 spray samples using the MCTD formulation showed that they could be stored at 4 and 25° C. for 12 months without significant change in $TCID_{50}$ titer. After storage at 37° C. for five weeks, the loss of virus activity was only 0.12 log (FIG. 7).

Discussion

Stabilizing excipients are used before spray drying to prevent degradation during processing and storage. Disaccharides are amongst the most frequently used excipients, with trehalose being a particularly common selection (see, Maa Y F, et al., (1999) *Pharmaceutical Research* 16:249-254; Tzannis S T, et al. (2000) *J Pharm Sci* 88:360-370; Burger J L, et al. (2008) *J Aeros Med Pulmon Drug Deli* 21: 25-34; Corbaniea E A, et al., (2007) *Vaccine* 25:8306-8317; Broadhead J, et al. (1994) *J Pharm Pharmacol* 46:458-67; Labrude P, et al. (1989) *J Pharm Sci* 78:223-239; and Bosquillon C, et al. (2001) *J Pharm Sci* 90: 2032-2041). However, the trehalose and sucrose-based powders are more hygroscopic, picking up moisture during handling in the laboratory environment that leads to degradation in physical properties of the powder and reduces the ease of dispersion. The sensitivity of powders to moisture uptake is important because the aerosol physical properties of inhalable dry powders are strongly dependent on moisture content; too much water can cause particle agglomeration, leading to reduced respirability.

Leucine and mannitol based formulations are the least hygroscopic. Mannitol is stable as a powder and resists moisture resorption at relatively high humidities. These characteristics make it an ideal substance to encapsulate for inhalation, for diagnostic and therapeutic purposes (see, NYK, Chan H K (2002) *J Pharm Pharmaceut Sci* 5(2):

162-168; Burger J L et al., (2008) *J Aeros Med Pulmon Drug Deli* 21: 25-34; Corbaniea E A, et al. (2007) *Vaccine* 25:8306-8317; Bosquillon C, et al. (2001) *J Pharm Sci* 90: 2032-2041; Glover W., et al. 2006 *Journal of aerosol medicine* 19: 522-532; and Costantino H R, et al. (2000) *J Pharm Sci* 87: 1406-1411). The inhalation of dry-powder mannitol alone causes a marked increase in MCC (mucociliary clearance) in the whole right lung and in all lung regions in both asthmatic and healthy subjects (see, Glover W., et al. 2006 *Journal of aerosol medicine* 19: 522-532; Daviskas E, et al. (1997) *Eu Respir J* 10: 2449-2454; Daviskas E, et al. (1999) *Am. J. Respir. Crit. Care Med* 159:1843-1848; Daviskas E, et al. (2001) *Chest* 119:414-421; Daviskas E, et al. (2005) *Respirology* 2005: 46-56; and Anderson S D, et al. (1997) *Am J REsir Crit Care Med* 156: 758-765). Inhalation of dry-powder mannitol was well tolerated by all subjects and induced only a mild cough which was reproduced on the control day (see, Glover W., et al. 2006 *Journal of aerosol medicine* 19: 522-532, and Anderson S D, et al. (1997) *Am J REsir Crit Care Med* 156: 758-765). This increases the advantage of using a mannitol-based spray drying formulation in the development of powder form vaccines. With the processing conditions used in the present study, the moisture content of the trehalose-based formulation was higher than the other tested formulations, while mannitol-based formulations typically resisted water absorbtion, even when exposed to conditions of high humidity, which will benefit applications in vaccine storage and clinical trials.

The glass transition temperature of the dry formulations is also strongly dependent on water content; just a few percent increase in the water content of sugar-based formulations can decrease the $T_g$ by several tens of degrees Celsius (see, Corbaniea E A, et al. (2007) *Vaccine* 25:8306-8317). Higher moisture content also results in decreased viral stability (see, Burger J L, et al. (2008) *J Aeros Med Pulmon Drug Deli* 21: 25-34, and Corbaniea E A, et al. (2007) *Vaccine* 25:8306-8317). Immobilization of the labile materials in amorphous glass is believed to be advantageous to maintain the activity of the incorporated molecules (see, Imamura K et al. (2001) *J Pharm Sci* 90:1955-1963). The resistance to crystallization can be evaluated by measuring the glass transition temperature, which is the temperature at which the transition from the glassy to the rubbery state or from a low molecular mobility to a high molecular mobility (and therefore, higher risk of crystallization) occurs. PVP and albumins are known to increase the glass transition temperature, which means that the formulations can be exposed to higher ambient temperatures before the glass transition occurs (see, Corbaniea E A, et al. (2007) *Vaccine* 25:8306-8317; Mahlin D, et al. (2006) *Int J Pharm* 321:78-85; and Zhang J, et al. (2001) *J Pharm Sci* 90:1375-1385). However, PVP as a stabilizer in the tested formulation did not appear to prevent loss of virus activity during the spray drying process.

Dextran has also been shown to prevent crystallization of spray-dried and freeze-dried excipients. Therefore, the mannitol-based formulation used in the present study, MCTD, includes two kinds of dextran as components. This formulation could increase the glass transition temperature of trehalose from 50.55 to 97.09° C. The formulation also generates a dry powder that inhibits re-crystallization of stabilizing sugars, preventing inactivation of incorporated labile materials, and its glass transition temperature does not decrease during storage at high humidity. Equally important as low hygroscopicity in formulation selection, since water molecules are known to increase the molecular mobility, is a high and non-shifting glass transition temperature during storage. With glass transition temperature of the formulations occurring at about 50° C. and higher, the powders and microparticles should be physically stable at temperatures up to about 40° C., as long as the powders are protected from moisture ingress. As mentioned above, the MCTD formulation showed no detectable decrease in IP<5 μm after storage at 37° C. for 28 days. The higher $T_g$ values measured for this formulation suggest that enhanced long-term thermostability may be possible.

These results show that MCTD is a good candidate for both live virus and placebo selections. MCTD is not only conducive to forming easily dispersed microparticles in dry processing, but also appears to be a good stabilizer formulation for the rAd35 vaccine vector virus. Combinations of small and high molecular weight sugar stabilizers help achieve optimized viral processing and storage stability, while mitigating the negative particle forming properties of trehalose. The other tested formulations did not retain activity as well as the MCTD formulation during the spray drying process, or at 37° C. in the 1-month stability test.

Materials and Methods

Chemicals

Leucine was bought from Spectrum, Gardena, Calif.; mannitol, sucrose, histidine, Trehalose were from J. T. Baker, Phillipsburg, N.J.; Dextran (M.W. 60,000-90,000) was from MP Biomedicals, Solon, Ohio; 13-Cyclodextrin was from TCI-GR, Kita-Ku, Tokyo, Japan; polyvinylpyrrolidone (PVP, M.W. 8,000, K16-18) was from ACROS, N.J.; Inositol was bought from EMD, Gibbstown, N.J.

CPS Disc Centrifuge

The size of rAd35 vaccine virus was measured by CPS Disc centrifuge (CPS Instruments, Inc., Stuart, Fla.). Sucrose (8% and 24%) in sample buffer was used for gradient solutions. CPSV95 software was set up for data collection, analysis and process control. The maximum speed was selected at 24000 rpm. The total injection volume for each analysis was 100 μL. A solution of PVC (20%, v/v) 0.377 Micro Calibration Standard was used for calibration.

Spray Drying

The spray drying powders were generated by a Bichi Mini Spray Dryer B-290. Nitrogen was used as drying and atomizing gas. Ten different feed solutions were prepared: mannitol; trehalose; leucine; mannitol mixed with leucine, sucrose, PVP or inositol; mannitol in PBS buffer; mannitol-cyclodextrin-trehalose-dextran (MCTD), and mannitol-trehalose-dextran-tween 80 (MTDT). Except leucine using 0.5%, the formulations were based on 10% solid of total volume. Formulations with the same concentrations without rAd35 were used for placebo tests. The inlet temperature was set at 65 to 125° C. and the drying gas flow rate at 439 to 538 L/h resulting in an outlet temperature of 34 to 50° C. The aspirator rate was 35 m$^3$/h. The spray drying process and subsequent powder aliquoting were executed in a Bio-Protect II hood (The Baker Co.). To minimize both environmental microbial contamination to the powder and small powder particles released to environment, the spray dryer was assembled with a PTFE outlet filter and a 0.2-μm EMFLON Filter (Pall Life Sciences, USA) fitted to the compressed air line.

Differential Scanning Calorimetry (DSC)

The thermodynamic behavior of the powders was determined on a DSC 823$^e$(METTLER TOLEDO, Switzerland). The cover of the crucible containing the powder sample was punched with a small hole before analysis. The sample (around 10 mg powder) was heated from 25° C. to 170° C. with a scanning rate of 10.0° C./min. The sample cell was purged with a nitrogen gas of 10.0 mL/min. The glass transition temperature ($T_5$) was recognized on the reversing heat flow curve as an endothermic shift of the baseline and determined as the midpoint of this transition by a STAReSW9.01 software (METTLER).

Particle Size Distribution, Polydispersity and Morphology

Particle size distributions were measured by laser diffraction (Mastersizer 2000, Malvern, Worcs, UK). The polydispersity of the powder was expressed by the span. Span=[D(v,90)−D(v,10)]/D(v,50), where D(v,90), D(v,10) and D(v,50) are the equivalent volume diameters at 90, 10 and 50% cumulative volume, respectively. The particle size of the primary powders was described by the volume median diameter (VMD), which is related to the mass median diameter (MMD) by the density of the particles (assuming a size independent density for the particles). A microscope (Axioskop 40, ZEISS) was used to examine particle morphology of spray dried powders. The mannitol powders were re-suspended in anhydrous methanol at around 20 mg/mL. A drop of this suspension was placed on a clean microscope slide. After 2 minutes, the slide was examined with the oil immersion objective (×100) and a 10× ocular. Re-suspension of trehalose powder in methanol was found to be impractical because of high solubility. For trehalose, the method of Tracy et al. (Tracy P H, Hetrick J H, Karenke W A (1951) *J. Dairy Sci* 34 (6):583-592) was modified as follows: about 20 mg of powder was mixed with 1 mL of Halocarbon 0.8 oil, and a drop of the suspension was examined with a cover slip.

TCID$_{50}$ Assay

Ad35 virus titers in the original feed solutions and in the corresponding powders were determined by titration in TCID$_{50}$ tests. The TCID titer value (tissue culture infectious dose) was determined by the greatest dilution at which cytopathic effects (CPE) were observed on human embryonic retinoblast cells (HER: 911 cells) in a TCID$_{50}$ assay. Briefly, the 911 cells were cultured in a 75 cm$^2$ flask containing Dulbecco's modified Eagle medium supplemented with 10% fetal bovine serum and antibiotics (penicillin and streptomycin). When cells were confluent, cells were detached using Trypsin-EDTA solution and the cell concentration was adjusted to 4×10$^5$ cells/mL. Cell suspension (100 μL) was seeded in one or two 96-well flat bottom tissue culture plates and incubated at 37° C. with 10% CO$_2$ for 4 hr. After cells were attached the media was removed and 160 μL of medium was dispensed into all the wells. Then 40 μL each of pre-diluted virus was added to 8 wells in the first column and subsequently 5-fold serial dilution was performed in the plates for dilutions ranging from 10$^{-1}$ to 10$^{-11}$ or 10$^{-7}$ to 10$^{-17}$, depending on the expected titer value, and the plates were incubated for 14 days. CPE was scored on day 14 and the virus titer was determined employing the Spearman-Karber formula as follows.

$$\text{Log TCID}_{50}/100 \ \mu L = X_0 - (d/2) + (d/n)\Sigma_{X_i}$$

Where '$X_0$' is the log$_{10}$ of the reciprocal of the highest dilution at which all testing columns are CPE positive, 'd' represent the log$_{10}$ value of the dilution factor (d=0.699 for 5-fold dilution factor) and 'n' is the number of wells for each dilution. '$\Sigma_{X_i}$' is the sum of all wells that give CPE, from the dilution '$X_0$', including CPE of dilution '$X_0$'. The resulting titer value was adjusted for initial dilutions and reported as TCID$_{50}$/mL.

Karl FischerTitration

The residual moisture content after spray drying and the water content after 2 to 6 hr storage in a humidity box (70%, humidity detector from VWR, USA), were evaluated by a TIM550 Karl Fischer (Radiometer Analytical) in a dry box. The samples (±30 mg) were resuspended in absolute, dry methanol (Phillipsburg, N.J.). After background standby, the titration started automatically. During this titration, water molecules react stoichiometrically with the AQUA STAR® CombiTitrant 5 (EMD) reagent; subsequently, the volume of CombiTitrant 5 used to reach the endpoint of titration is used to calculate the percentage of water present in the sample (1 mL CombiTitrant 5=5 mg water). All titrations were performed in triplicate.

The invention claimed is:

1. An immunogenic composition, comprising:
   one or more live viruses in a powder formulation spray dried from a composition comprising mannitol at 50-100 mg/ml, cyclodextrin at 0.2-1 mg/ml, trehalose at 0.5-5 mg/ml, and dextran at 0.5-5 mg/ml, wherein the one or more live viruses encode one or more *Mycobacterium tuberculosis* antigens.

2. The immunogenic composition of claim 1 wherein said powder formulation is spray dried from a composition which comprises 100 mg/ml mannitol at 0.2 mg/ml cyclodextrin, 2 mg/ml trehalose, and 1 mg/ml dextran.

3. The immunogenic composition of claim 1 wherein said cyclodextrin includes one or more of α- or β- or γ-cyclodextrin.

4. The immunogenic composition of claim 1 wherein said dextran has a molecular weight ranging from 25K to 500K.

5. The immunogenic composition of claim 4 wherein said dextran has molecular weight ranging from 40K to 90K.

6. The immunogenic composition of claim 1 further comprising buffering agents.

7. The immunogenic composition of claim 1 wherein said virus is non-replicating or replication deficient.

8. The immunogenic composition of claim 1 wherein said virus is an adenovirus.

9. The immunogenic composition of claim 1 wherein said powder formulation has a median volume diameter of 3.2-3.5 μm.

10. A method of forming an immunogenic composition, comprising:
    spray drying one or more live viruses from a composition comprising mannitol at 50-100 mg/ml, cyclodextrin at 0.2-1 mg/ml, trehalose at 0.5-5 mg/ml, and dextran at 0.5-5 mg/ml to form a spray dried powder containing said one or more live viruses, wherein the one or more live viruses encode one or more *Mycobacterium tuberculosis* antigens.

11. The method of claim 10 wherein said virus is non-replicating or replication deficient.

12. The method of claim 10 wherein said virus is an adenovirus.

13. The immunogenic composition of claim 2, further comprising 0.78 mg/ml histidine.

14. The immunogenic composition of claim 1, wherein the one or more *Mycobacterium tuberculosis* antigens are chosen from: Rv0079, Rv0101, Rv0125, Rv0170, Rv0198c, Rv0211, Rv0227c, Rv0243, Rv0251c, Rv0282, Rv0283, Rv0284, Rv0285, Rv0286, Rv0287, Rv0288, Rv0289, Rv0290, Rv029, Rv0350, Rv0351, Rv0383c, Rv0384c, Rv0450c, Rv0467, Rv0468, Rv0503c, Rv0569, Rv0572c, Rv0574c, Rv0588, Rv0628c, Rv0685, Rv0754, Rv0798c, Rv0824c, Rv0847, Rv0867c, Rv0885, Rv1006, Rv1009, Rv1057, Rv1094, Rv1124, Rv1130, Rv1131, Rv1169c, Rv1174c, Rv1182, Rv1186c, Rv1187, Rv1188, Rv1196, Rv1221, Rv1347c, Rv1348, Rv1349, Rv1411c, Rv1436, Rv1461, Rv1462, Rv1464, Rv1465, Rv1466, Rv1477, Rv1478, Rv1594, Rv1636, Rv1733c, Rv1734c, Rv1735c, Rv1736c, Rv1737c, Rv1738, Rv1793, Rv1812c, Rv1813c, Rv1876, Rv1884c, Rv1886c, Rv1908c, Rv1926c, Rv1980c, Rv1986, Rv1996, Rv1997, Rv1998c, Rv2004c, Rv2005c, Rv2006, Rv2007c, Rv2008c, Rv2011c, Rv2028c, Rv2029c, Rv2030c, Rv2031c, Rv2032, Rv2110c, Rv2123, Rv2140c, Rv2182c, Rv2224c, Rv2244, Rv2245, Rv2246, Rv2251, Rv2377c, Rv2378c, Rv2380c, Rv2381c, Rv2382c, Rv2383c, Rv2386c, Rv2389c, Rv2428, Rv2429, Rv2430c, Rv2450c, Rv2457c, Rv2466c, Rv2510c, Rv2515c, Rv2516c, Rv2557, Rv2590, Rv2620c, Rv2621c, Rv2622, Rv2623, Rv2625c, Rv2626c, Rv2627c, Rv2628, Rv2629, Rv2657c, Rv2659c, Rv2660, Rv2710, Rv2744c, Rv2780, Rv2833c, Rv2856, Rv2869c, Rv2875, Rv2930, Rv2999, Rv3126c, Rv3127, Rv3129, Rv3130c, Rv3131, Rv3132c, Rv3133c, Rv3134c, Rv3139, Rv3140, Rv3173c, Rv3229c, Rv3250c, Rv3251c, Rv3283, Rv3290c, Rv3347c, Rv3372, Rv3406, Rv3516, Rv3546, Rv3570c, Rv3593, Rv3597c, Rv3616c, Rv3619c, Rv3660c, Rv3763, Rv38G4c, RV3812, RV3833, RV3839, RV3840, RV3841, Rv3871, Rv3873, Rv3874, Rv3875, Rv3876, Rv3878, and Rv3879c.

15. The method of claim 10, wherein the one or more *Mycobacterium tuberculosis* antigens are chosen from: Rv0079, Rv0101, Rv0125, Rv0170, Rv0198c, Rv0211, Rv0227c, Rv0243, Rv0251c, Rv0282, Rv0283, Rv0284, Rv0285, Rv0286, Rv0287, Rv0288, Rv0289, Rv0290, Rv029, Rv0350, Rv0351, Rv0383c, Rv0384c, Rv0450c, Rv0467, Rv0468, Rv0503c, Rv0569, Rv0572c, Rv0574c, Rv0588, Rv0628c, Rv0685, Rv0754, Rv0798c, Rv0824c, Rv0847, Rv0867c, Rv0885, Rv1006, Rv1009, Rv1057, Rv1094, Rv1124, Rv1130, Rv1131, Rv1169c, Rv1174c, Rv1182, Rv1186c, Rv1187, Rv1188, Rv1196, Rv1221, Rv1347c, Rv1348, Rv1349, Rv1411c, Rv1436, Rv1461, Rv1462, Rv1464, Rv1465, Rv1466, Rv1477, Rv1478, Rv1594, Rv1636, Rv1733c, Rv1734c, Rv1735c, Rv1736c, Rv1737c, Rv1738, Rv1793, Rv1812c, Rv1813c, Rv1876, Rv1884c, Rv1886c, Rv1908c, Rv1926c, Rv1980c, Rv1986, Rv1996, Rv1997, Rv1998c, Rv2004c, Rv2005c, Rv2006, Rv2007c, Rv2008c, Rv2011c, Rv2028c, Rv2029c, Rv2030c, Rv2031c, Rv2032, Rv2110c, Rv2123, Rv2140c, Rv2182c, Rv2224c, Rv2244, Rv2245, Rv2246, Rv2251, Rv2377c, Rv2378c, Rv2380c, Rv2381c, Rv2382c, Rv2383c, Rv2386c, Rv2389c, Rv2428, Rv2429, Rv2430c, Rv2450c, Rv2457c, Rv2466c, Rv2510c, Rv2515c, Rv2516c, Rv2557, Rv2590, Rv2620c, Rv2621c, Rv2622, Rv2623, Rv2625c, Rv2626c, Rv2627c, Rv2628, Rv2629, Rv2657c, Rv2659c, Rv2660, Rv2710, Rv2744c, Rv2780, Rv2833c, Rv2856, Rv2869c, Rv2875, Rv2930, Rv2999, Rv3126c, Rv3127, Rv3129, Rv3130c, Rv3131, Rv3132c, Rv3133c, Rv3134c, Rv3139, Rv3140, Rv3173c, Rv3229c, Rv3250c, Rv3251c, Rv3283, Rv3290c, Rv3347c, Rv3372, Rv3406, Rv3516, Rv3546, Rv3570c, Rv3593, Rv3597c, Rv3616c, Rv3619c, Rv3660c, Rv3763, Rv38G4c, RV3812, RV3833, RV3839, RV3840, RV3841, Rv3871, Rv3873, Rv3874, Rv3875, Rv3876, Rv3878, and Rv3879c.

\* \* \* \* \*